United States Patent [19]
Cooper et al.

[11] Patent Number: 6,093,201
[45] Date of Patent: Jul. 25, 2000

[54] BIOCOMPATIBLE ABSORBABLE POLYMER PLATING SYSTEM FOR TISSUE FIXATION

[75] Inventors: Kevin L. Cooper, Warren; David W. Overaker, Annandale, both of N.J.

[73] Assignee: Ethicon, Inc., Somerville, N.J.

[21] Appl. No.: 09/233,569

[22] Filed: Jan. 19, 1999

[51] Int. Cl.[7] .......................... A61B 17/04; A61B 17/56
[52] U.S. Cl. .............................................. 606/232; 606/69
[58] Field of Search ................................ 606/69, 70, 71, 606/61, 60, 232

[56] References Cited

U.S. PATENT DOCUMENTS

| | | | |
|---|---|---|---|
| 4,905,680 | 3/1990 | Tunc | 606/69 |
| 5,002,544 | 3/1991 | Klaue et al. | 606/69 |
| 5,057,111 | 10/1991 | Park | 606/70 |
| 5,084,051 | 1/1992 | Tormala | 606/77 |
| 5,676,667 | 10/1997 | Hausman | 606/73 |

*Primary Examiner*—Gary Jackson
*Attorney, Agent, or Firm*—Hal Woodrow

[57] ABSTRACT

An absorbable biocompatible polymeric plate is described. The plate has channels on its top surface and through its thickness for receiving sutures to secure soft tissue proximally to the device. The plate also has notches on its bottom surface for added security of soft tissue when conditions require the surgeon to attach tissue beneath the plate.

21 Claims, 3 Drawing Sheets

BIOCOMPATIBLE ABSORBABLE POLYMER PLATING SYSTEM FOR TISSUE FIXATION

FIELD OF THE INVENTION

The general field to which the invention relates is absorbable polymer plates. Specifically, absorbable polyester matrices for use in a plating system for the fixation of bone and cartilage, especially hard tissue of the cranium, face and other plastic/reconstructive procedures.

BACKGROUND OF THE INVENTION

Synthetic absorbable biocompatible polymers are well known in the art. Such polymers are typically used to manufacture medical devices, which are implanted in body tissue and absorb over time. Synthetic absorbable biocompatible polymers include homopolymers, copolymers (random, block, segmented and graft) of monomers such as glycolic acid, glycolide, lactic acid, lactide (d, l, meso and mixtures thereof), $\epsilon$-caprolactone, trimethylene carbonate and p-dioxanone. Numerous U.S. Patents describe these polymers including U.S. Pat. Nos. 5,431,679; 5,403,347; 5,314,989; 5,431,679; 5,403,347; and 5,502,159.

Plating systems comprising such polymers have also been described. U.S. Pat. No. 4,905,680 describes an absorbable bone plate having an elongated body with lower and upper surfaces and a plurality of screw holes where the width of the plate and its thickness is extended around the screw holes to add reinforcement so that stresses surrounding the screw holes are not significantly greater than those developed in any unreinforced area of the plate.

U.S. Pat. No. 5,057,111 describes a non-stress shielding bone fracture healing compression plate with at least two openings to attach it to the bone tissue where at least one opening is designed with a relaxation section. When the plate begins to creep under load the stresses can be transferred to the bone so that stress shielding will not occur.

U.S. Pat. No. 5,275,601 describes a self locking absorbable bone screw and plate system where the head has three dimensional corrugations that when driven into the plate locks it into similar corrugations found on the plate. The plate additionally has undercuts or three-dimensional conical or pyramidal elements to decrease contact area between the bone and the plate.

U.S. Pat. Nos. 5,290,281 and 5,607,427 describe a surgical plating system that includes a thermoplastic, absorbable plate with a plurality of concave formations and through-bore holes arranged in an alternating fashion along the plate; fasteners that are inserted through the bore holes to secure the plate to the tissue; and a heating wand with a tip adapted to mate with the concave formations to heat and bend the plate to conform it to the contours of the tissue.

U.S. Pat. No. 5,569,250 describes a biocompatible osetosynthesis plate secured to a plurality of bone portions. The plate has an elongated section with a top and bottom face, at least one fastener opening between the faces and means for permitting additional fastener openings to be formed during the surgical procedure. The plate additionally can be converted from one thermochemical state to another by application of heat to deform it prior to fixation. The plates also have raised surfaces or rails disposed upon the top face to enhance rigidity.

Unfortunately, these patents do not recognize the need for a device that allows a method by which to secure soft tissue to the plate. This is critical, especially in plastic reconstructive procedures where soft tissue needs to be reattached near its original anatomical position to provide proper support during healing and improved post-surgical cosmesis.

The surgical plates of the present invention provide means to the surgeon to secure soft tissue to the plating system.

SUMMARY OF THE INVENTION

We have discovered an absorbable polymer plating system that provides means by which to secure soft tissue to the plates.

In one embodiment, a biocompatible plate is provided that has an upper surface, a lower surface, and fastener openings extending through the plates from the upper surface to the lower surface wherein the plate has channels for attaching sutures to the plate thereby allowing the suture to closely nestle against the plate for better post-surgical cosmesis.

In another embodiment, a biocompatible plate is provided that has an upper surface, a lower surface, and fastener openings extending through the plates from the upper surface to the lower surface wherein the plate has risers extending from the lower surface.

The foregoing and other features and advantages of the invention will become more apparent from the following description and accompanying examples.

DETAILED DESCRIPTION OF THE INVENTION

Figure 1:
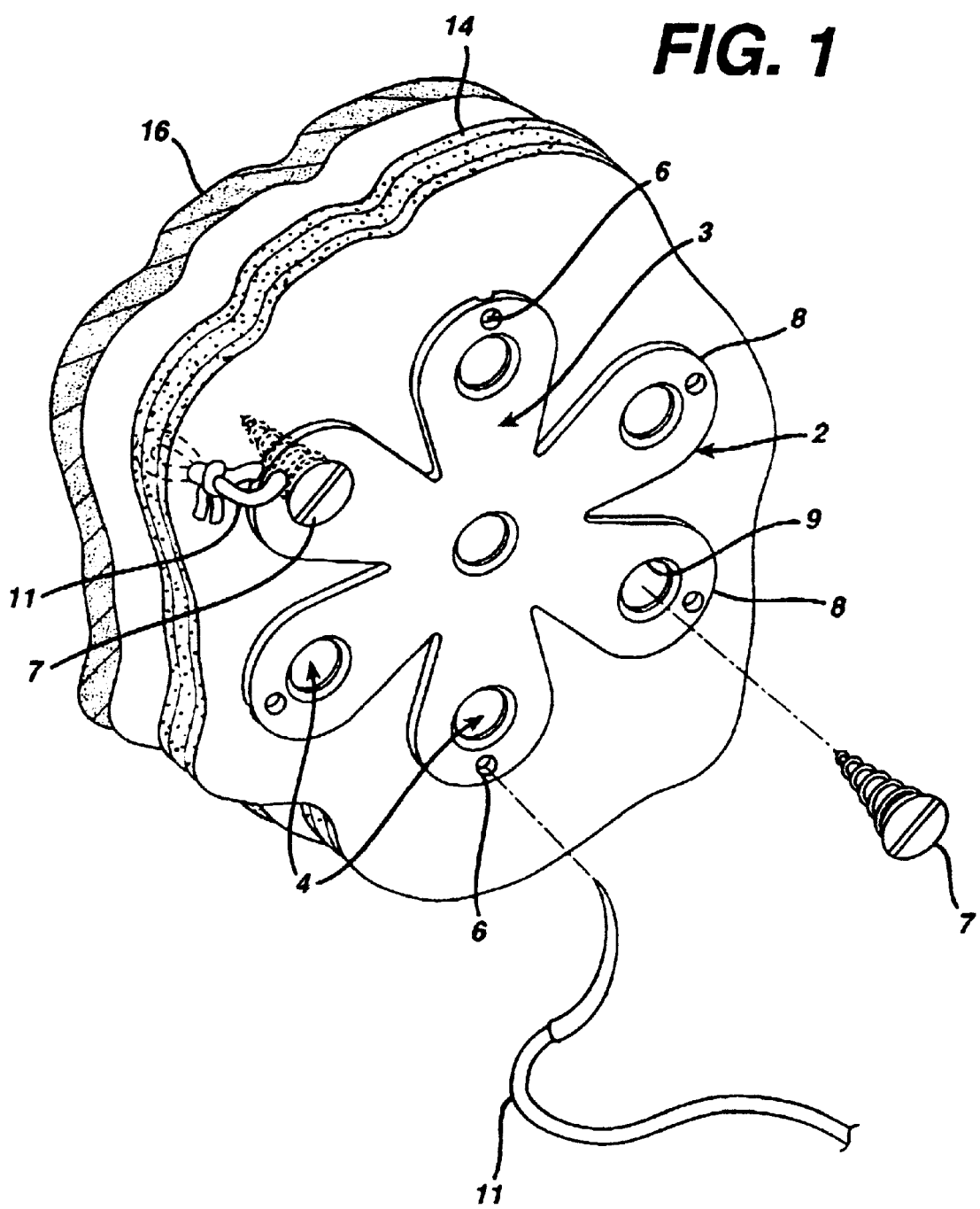
FIG. 1 is a perspective view of the upper surface of a biocompatible, absorbable plating device of the present invention.
Figure 2:
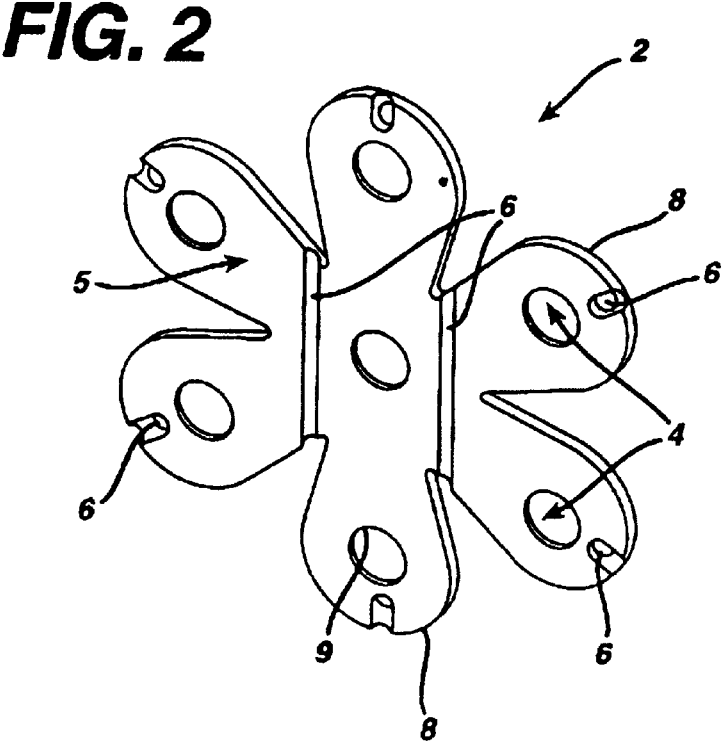
FIG. 2 is a perspective view of the lower surface of a biocompatible, absorbable plating device of the present invention.
Figure 3:
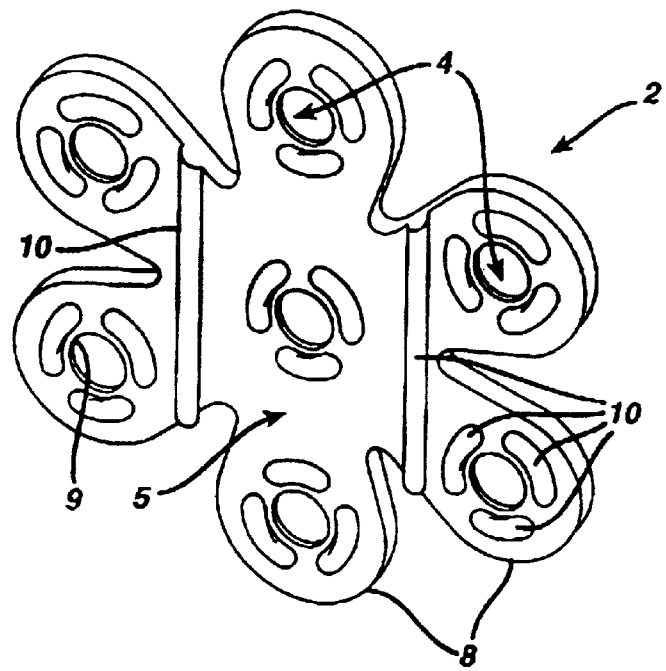
FIG. 3 is a perspective view of the lower surface of an alternative embodiment of a biocompatible, absorbable plating device of the present invention.

As is illustrated in FIGS. 1–3 the present invention discloses a plate 2 made of bioabsorbable material consisting of one or a plurality of fastener openings 4 extending through the upper surface 3 to the lower surface 5 of the plate 2. Fastener 7 may be passed through the fastener openings 4 to attach the plate 2 into hard tissue such as bone 16. The plates illustrated in FIGS. 1–3 have multiple lobes 8. However, the plates 2 used in the present invention may have a variety of shapes such as multi-lobed plates (illustrated in FIGS. 1–3), I, T, Y, L, H, X, square, triangular, or circular (as are illustrated in U.S. Pat. No. 5,569,250 hereby incorporated by reference herein). It is preferred, that the inner surface 9 of the fastener openings 4 be sloped to mate with a conical surface on the head of the fastener 7 such that said head may be flush with the upper surface 3 of the plate 2 when deployed.

Figure 4:
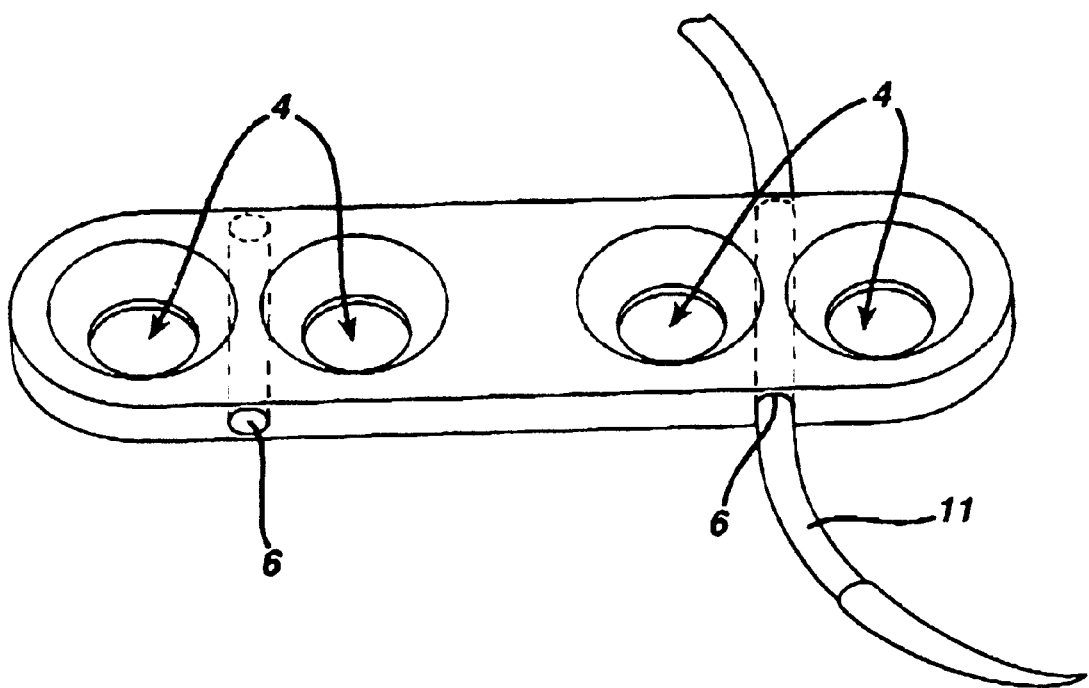
FIG. 4 is a perspective view of the upper surface of another alternative embodiment of a biocompatible, absorbable plating device of the present invention.

In one embodiment of the present invention, illustrated in FIGS. 1, 2 and 4 the plate 2 has one or more channels 6 through which sutures 11 may be placed to use in anchoring tissue 14 to the plate 2. These sutures 11 of course could be pre-threaded into the plates prior to use to facilitate ease of use in surgical procedures. As is shown in FIG. 1 these channels may extend only part way across and through the plate 2 or may traverse the plate (externally or internally) as shown in FIGS. 2 and 4. These plates are particularly well adapted to attaching tissue such as dermis, muscle or tendon tissue to a surface of the plate 2. These plates 2 would be especially desirable for use in facial reconstruction.

In another embodiment, illustrated in FIG. 3, the plate 2 has protrusions or risers 10 extending from the lower surface 5 of the plate 2 which serve to capture and provide a space for the tissue underneath the plate 2 when it is fastened to bone. The risers 10 may have a variety of shapes and be positioned in various patterns to facilitate tissue reattachment and maintenance of tissue viability. The tissue directly beneath the riser will be trapped between the bone and the riser 10. The trapped tissue will be secured in position, which is one method for reattaching ligaments to bone. The tissue that occupies the space created by the riser between the lower surface 5 of the plate 2 and the bone will be capable of remaining viable. Additionally, channels may also be used with the risers to secure to the upper and lower surface of the plates.

The plates of the present invention may be made from a variety of biocompatible materials. These biocompatible materials may be non-absorbable or absorbable. The non-absorbable materials include metals and polymers. Suitable biocompatible metals include, but are not limited to metals selected from the group consisting of stainless steel, titanium and tantalum.

Examples of suitable biocompatible non-absorbable polymers with relatively low chronic tissue response include but are not limited to polymers selected from the group consisting of polyurethanes, polyolefins, polyesters, poly(meth)acrylates, polyvinyl fluorides, nylons and combinations thereof. Suitable polymers include but are not limited to polymers selected from the group consisting of polyolefins (such as polyethylene and polypropylene including atactic, isotactic, syndiotactic, and blends thereof as well as, polyisobutylene and ethylene-alphaolefins copolymers); polyesters (such as polyethylene terephthalate and polybutylene terephthalate); acrylic polymers and copolymers, vinyl halide polymers and copolymers (such as polyvinyl chloride); polyvinyl ethers (such as polyvinyl methyl ether); polyvinylidene halides (such as polyvinylidene fluoride and polyvinylidene chloride); polyacrylonitrile; polyvinyl ketones; polyvinyl aromatics (such as polystyrene); polyvinyl esters (such as polyvinyl acetate); copolymers of vinyl monomers with each other and olefins, (such as etheylene-methyl methacrylate copolymers, acrylonitrile-styrene copolymers, ABS resins and ethylene-vinyl acetate copolymers); polyamides (such as nylon 4, nylon 6, nylon 66, nylon 610, nylon 11, nylon 12 and polycaprolactam); alkyd resins; polycarbonates; polyoxymethylenes; polyimides; polyethers; epoxy resins, polyurethanes; rayon; and rayon-triacetate. Polyamides for the purpose of this application would also includes polyamides of the form-NH—(CH$_2$)$_n$—CO— and NH—(CH$_2$)$_x$—NH—CO—(CH$_2$)$_y$—CO, wherein n is preferably an integer in from 6 to 13; x is an integer in the range of form 6 to 12; and y is an integer in the range of from 4 to 16. The list provided above is illustrative but not limiting.

Suitable biocompatible absorbable materials from which the plate may be formed include biocompatible absorbable polymers selected from the group consisting of: aliphatic polyesters; polyorthoesters; polyanhydrides; polycarbonates; polyurethanes; polyamides; polyalkylene oxides; and combinations thereof. The orthopedic plate of the present invention can also be formed from absorbable glasses or ceramics comprising calcium phosphates and other biocompatible metal oxides (i.e., CaO). The plate of the present invention can further comprise combination of absorbable ceramics, glasses and polymers.

In a preferred embodiment, the orthopedic plate will be formed from an aliphatic polyester(a) and blends thereof. The aliphatic polyesters are typically synthesized in a ring opening polymerization. Suitable monomers include but are not limited to lactic acid, lactide (including L-, D-, meso and D,L mixtures), glycolic acid, glycolide, ε-caprolactone, p-dioxanone (1,4-dioxan-2-one), trimethylene carbonate (1,3-dioxan-2-one), delta-valerolactone, beta-butyrolactone, epsilon-decalactone, 2,5-diketomorpholine, pivalolactone, alpha, alpha-diethylpropiolactone, ethylene carbonate, ethylene oxalate, 3-methyl-1,4-dioxane-2,5-dione, 3,3-diethyl-1,4-dioxan-2,5-dione, gamma-butyrolactone, 1,4-dioxepan-2-one, 1,5-dioxepan-2-one, 6,6-dimethyl-dioxepan-2-one, 6,8-dioxabicycloctane-7-one and combinations thereof.

These monomers are generally polymerized in the presence of an organometallic catalyst and an initiator at elevated temperatures. The organometallic catalyst is preferably tin based, e.g., stannous octoate, and is present in the monomer mixture at a molar ratio of monomer to catalyst ranging from about 10,000/1 to about 100,000/1. The initiator is typically an alkanol (including diols and polyols), a glycol, a hydroxyacid, or an amine, and is present in the monomer mixture at a molar ratio of monomer to initiator ranging from about 100/1 to about 5000/1. The polymerization is typically carried out at a temperature range from about 80° C. to about 240° C., preferably from about 100° C. to about 220° C., until the desired molecular weight and viscosity are achieved.

The polymer blends of the present invention are manufactured in a conventional manner, preferably in the following manner. The homopolymers and copolymers, prepared as described above, are individually charged into a conventional mixing vessel or reactor vessel having a conventional mixing device mounted therein, such as an impeller or equivalents thereof. Then, the polymers and copolymers are mixed at a temperature of about 100° C. to about 230° C., more preferably from about 160° C. to about 200° C., for about 5 to about 90 minutes, more preferably for about 10 to about 45 minutes, until a uniformly dispersed polymer blend is obtained. Then, the polymer blend is further processed by removing it from the mixing device, cooling to room temperature, grinding, and drying under pressures below atmospheric at elevated temperatures for a period of time using conventional apparatuses and processes.

Under the above described conditions, the polymers and blends composed of glycolide, ε-caprolactone, p-dioxanone, lactide and trimethylene carbonate will typically have a weight average molecular weight of about 20,000 grams per mole to about 300,000 grams per mole, more typically about 40,000 grams per mole to about 200,000 grams per mole, and preferably about 60,000 grams per mole to about 150,000 grams per mole. These molecular weights provide an inherent viscosity between about 0.5 to about 4.0 deciliters per gram (dL/g), more typically about 0.7 to about 3.5 dL/g, and most preferably about 1.0 to about 3.0 dL/g as measured in a 0.1 g/dL solution of hexafluoroisopropanol (HFIP) at 25° C. Also, it should be noted that under the above-described conditions, the residual monomer content would be less than about 5 weight percent.

Articles such as the absorbable plates of the present invention are molded from the polymers and blends of the present invention by use of various injection and extrusion molding equipment equipped with dry nitrogen atmospheric chamber(s) at temperatures ranging from about 100° C. to about 230° C., more preferably 140° C. to about 200° C., with residence times of about 1 to about 20 minutes, more preferably about 2 to about 10 minutes.

In addition, the absorbable plates of the present invention can be molded from the polymers and blends of the present invention by use of compression molding equipment equipped with a nitrogen chamber to maintain an inert atmosphere at temperatures ranging from about 100° C. to about 230° C., more preferably 140° C. to about 200° C., with residence times of about 1 to about 20 minutes, more preferably about 2 to about 10 minutes at a pressure of about 100 lbs. to about 25000 lbs., more preferably 1000 lbs. to about 10000 lbs., to form plaques. The plaques would be then machined using various machining equipment to form various shaped articles.

The plate after molding will be sterilized by conventional means and packaged in an appropriate container for use in a surgical setting.

In another embodiment of the present invention, the plate is coated with or if made from a polymer or polymer blend can also contain a pharmaceutically active compound or therapeutic agent. The variety of different therapeutic agents that can be used in conjunction with the polymers of the present invention is vast. In general, therapeutic agents which may be administered via this invention include, without limitation: antiinfectives such as antibiotics and antiviral agents; analgesics and analgesic combinations; antiinflammatory agents; hormones such as steroids; bone regenerating growth factors; and naturally derived or genetically engineered proteins, polysaccharides, glycoproteins, or lipoproteins.

Matrix formulations may be formulated by mixing one or more therapeutic agents with a polymer (such as an aliphatic polyester). The therapeutic agent, may be present as a liquid, a finely divided solid, or any other appropriate physical form. Typically, but optionally, the matrix will include one or more additives, such as diluents, carriers, excipients, stabilizers or the like.

The amount of therapeutic agent will depend on the particular drug being employed and medical condition being treated. Typically, the amount of drug represents about 0.001% to about 70%, more typically about 0.001% to about 50%, most typically about 0.001% to about 20% by weight of the matrix.

The quantity and type of drug incorporated into the delivery matrix will vary depending on the release profile desired and the amount of drug employed.

Upon contact with body fluids, aliphatic polyesters undergoes gradual degradation (mainly through hydrolysis) with concomitant release of the dispersed drug for a sustained or extended period. This can result in prolonged delivery (over, say 1 to 5,000 hours, preferably 2 to 800 hours) of effective amounts (say, 0.0001 mg/kg/hour to 10 mg/kg/hour) of the drug. This dosage form can be administered as is necessary depending on the subject being treated, the severity of the affliction, the judgment of the prescribing physician, and the like.

Following this or similar procedures, those skilled in the art will be able to prepare a variety of formulations.

In another embodiment of the present plate invention, a biocompatible dye could be added to the polymer used to make the device during processing in order to make it more visible in the surgical field. Additionally, radio-opaque markers may be added to the plate to allow imaging after implantation.

The following non-limiting examples are illustrative of the principles and practice of this invention. Numerous additional embodiments within the scope and spirit of the invention will become apparent to those skilled in the art.

EXAMPLES

The examples describe a biocompatible, absorbable plating system that comprises a polymer, copolymer or polymer blend that has unique soft tissue fixation characteristics.

In the synthetic process, the high molecular weight aliphatic polyesters are prepared by a method consisting of reacting lactone monomers via a ring opening polymerization at temperatures of 100° C. to 230° C. for 2 to 24 hours under an inert nitrogen atmosphere until the desired molecular weight and viscosity are achieved.

The polymer blends of the present invention are prepared by individually charging the synthesized aliphatic homo- and co-polymers into a conventional mixing vessel. The homopolymers and copolymers are mixed at a temperature of 100° C. to 230° C., for 5 to 90 minutes until a uniformly dispersed polymer blend is obtained.

The absorbable plates of the present invention are molded from the polymers and blends of the present invention by use of various injection and extrusion molding equipment equipped with dry nitrogen atmospheric chamber(s) at temperatures ranging from 100° C. to 230° C., with residence times of 1 to 20 minutes.

In addition, the absorbable plates of the present invention can be molded from the polymers and blends of the present invention by use of compression molding equipment equipped with a nitrogen chamber to maintain an inert atmosphere at temperatures ranging from 100° C. to about 230° C., with residence times of about 1 to about 20 minutes at a pressure of 5000 lbs. to form plaques. The plaques are then machined using various machining equipment to from various shaped articles.

In the examples which follow, the blends, polymers and monomers were characterized for chemical composition and purity (NMR, FT-IR), thermal analysis (DSC), melt rheology (melt stability and viscosity), molecular weight (inherent viscosity), and baseline mechanical properties (Instron stress/strain).

Inherent viscosities (I.V., dL/g) of the blends and polymers were measured using a 50 bore Cannon-Ubbelhode dilution viscometer immersed in a thermostatically controlled water bath at 25° C. utilizing chloroform or HFIP as the solvent at a concentration of 0.1 g/dL.

Several examples will be described in the following few pages. Parts and percentages where used are parts and percentages as specified as weight or moles.

Example 1

Synthesis of a 85:15 (mol/mol) poly(lactide-co-glycolide) copolymer

The method described below and utilized in this example is similar to those described in U.S. Pat. Nos. 4,643,191, 4,653,497, 5,007,923, 5,047,048 which are incorporated by reference, and is known to those skilled in the art.

To a flame dried 500 mL 1-neck round bottom flask equipped with an overhead mechanical stirrer and nitrogen inlet, 268 grams (1.86 moles) of L(−) lactide, 38.4 grams (0.330 moles) of glycolide, 0.53 grams ($7 \times 10^{-3}$ moles) of glycolic acid initiator, and 131 microliters of a 0.33 M solution of stannous octoate catalyst are added.

The assembly was then placed in a high temperature oil bath at 185° C. The stirred monomers quickly began to melt.

The low viscosity melt quickly increased in viscosity. Mechanical stirring of the high viscosity melt was continued for a total reaction time of 4 hours.

The 85:15 (mol/mol) poly(lactide-co-glycolide) copolymer is removed from the bath, cooled to room temperature under a stream of nitrogen, isolated and ground. The polymer was then dried under vacuum at 110° C. for 24 hours. Inherent viscosity using HFIP as a solvent is 1.90 dL/g.

Example 2

Injection molding a circular plate (of FIG. 1) of a 85:15 poly(lactide-co-glycolide) copolymer 1.5 Kg of the polymer as formed in Example 1 is added to a nitrogen purged hopped of a 28 ton Engel injection molder equipped with an 18 mm diameter barrel to form a circular plate as shown in FIG. 1. Two heating zones of 170° C., and 170° C. were employed to melt the blend as it entered the barrel. A nozzle temperature of 170° C. with an injection pressure of 500 psi and a speed of 2 in/s were used to feed the molten material down the barrel. Each injection produced a single part in a single cavity mold. A temperature of 30° C. was used in the mold to optimize the stress levels in the part. Using this process 2 parts are formed per minute.

Example 3

Compression molding and machining a circular plate (of FIG. 1) of a 85:15 poly(lactide-co-glycolide) copolymer 32 grams of a 85:15 poly(lactide-co-glycolide) copolymer is placed on a 6"×6" metal platen. A 6"×6" metal schimm is placed around the polymer and then a second 6"×6" metal platen is placed on top of the other metal platen, the schimm and the polymer. The entire assembly is then placed in a Tetrahedron compression molding press equipped with a nitrogen chamber to maintain an inert atmosphere. The temperature of the press is slowly ramped up to 185° C. After 10 minutes at 185° C., the polymer becomes molten and 5000 lbs. of pressure is slowly applied. The pressure and temperature are maintained for ten minutes. The press is then cooled to room temperature and the plaque is removed from the platen assembly. The plaque is then machined into various plate geometries and sizes.

Example 4

A circular burr hole cover plate (as illustrated in FIG. 1) is manufactured from the matrix described in Example 1 by the injection molding process described in Example 2. The plate is immersed in a vessel containing a biocompatible heat transfer medium (i.e. warm water) at a temperature of about 50–60° C. The surgeon shapes the plate by bending it without causing damage to the plate. The surgeon then secures the soft tissue to the plate and then the plate to the fracture site in a conventional manner using conventional fasteners (i.e. screws, rivets).

We claim:

1. A biocompatible plate having an upper surface, a lower surface, fastener openings extending through the plate from the upper surface to the lower surface; and one or more channels traversing the plate for attaching at least one suture to the plate.

2. The biocompatible plate of claim 1 wherein the channel traverses the lower surface of the biocompatible plate.

3. The biocompatible plate of claim 1 wherein the channel internally traverses the biocompatible plate.

4. The biocompatible plate of claim 1 wherein the plate is made from a biocompatible material selected from the group consisting of aliphatic polyesters; polyorthoesters; polyanhydrides; polycarbonates; polyurethanes; polyamides; polyalkylene oxides; absorbable glasses or ceramics comprising calcium phosphates; biocompatible metal oxides; and combinations thereof.

5. The biocompatible plate of claim 4 wherein the biocompatible plate is made from biocompatible aliphatic polyesters.

6. The biocompatible aliphatic polyester of claim 5 wherein the aliphatic polyester is selected from the group consisting of polylactide, polyglycolide, poly-1,4-dioxan-2-one, polytrimethylene carbonate and poly($\epsilon$-caprolactone), copolymers and blends thereof.

7. The biocompatible plate of claim 1 wherein the plate has a shape selected from the group consisting of multilobed, I, T, Y, L, H, X, square, triangular, and circular.

8. The biocompatible plate of claim 1 wherein additionally present is a pharmaceutically active compound selected from the group consisting of antiinfectives; analgesics and analgesic combinations; antiinflammatory agents; hormones; growth factors; and naturally derived or genetically engineered proteins, polysaccharides, glycoproteins, or lipoproteins.

9. The biocompatible plate of claim 1 wherein additionally present in the biocompatible plate is a radio-opaque marker.

10. The biocompatible plate of claim 1 wherein a suture is attached to the biocompatible plate.

11. A biocompatible plate having an upper surface, a lower surface, fastener openings extending through the plate from the upper surface to the lower surface, risers extending from the lower surface; and one or more channels for attaching at least one suture to the plate.

12. The biocompatible plate of claim 11 wherein the plate is made from a biocompatible material selected from the group consisting of aliphatic polyesters; polyorthoesters; polyanhydrides; polycarbonates; polyurethanes; polyamides; polyalkylene oxides; absorbable glasses or ceramics comprising calcium phosphates; biocompatible metal oxides; and combinations thereof.

13. The biocompatible plate of claim 12 wherein the biocompatible plate is made from biocompatible aliphatic polyesters.

14. The biocompatible aliphatic polymer of claim 13 wherein the aliphatic polyester is selected from the group consisting of polylactide, polyglycolide, poly-1,4-dioxan-2-one, polytrimethylene carbonate and poly($\epsilon$-caprolactone), copolymers and blends thereof.

15. The biocompatible plate of claim 11 wherein the plate has a shape selected from the group consisting of multilobed, I, T, Y, L, H, X, square, triangular, and circular.

16. The biocompatible plate of claim 11 wherein the channel extends part way across a surface of the plate and through the plate.

17. The biocompatible plate of claim 11 wherein the channel traverses the lower surface of the biocompatible plate.

18. The biocompatible plate of claim 11 wherein the channel internally traverses the biocompatible plate.

19. The biocompatible plate of claim 11 wherein additionally present is a pharmaceutically active compound selected from the group consisting of antiinfectives; analgesics and analgesic combinations; antiinflammatory agents; hormones; growth factors; and naturally derived or genetically engineered proteins, polysaccharides, glycoproteins, or lipoproteins.

20. The biocompatible plate of claim 11 wherein additionally present in the biocompatible plate is a radio-opaque marker.

21. The biocompatible plate of claim 11 wherein a suture is attached to the biocompatible plate.

* * * * *